United States Patent
Divi et al.

(10) Patent No.: US 8,378,111 B2
(45) Date of Patent: Feb. 19, 2013

(54) PROCESS FOR THE RESOLUTION OF (R,S)-NICOTINE

(75) Inventors: Murali Krishna Prasad Divi, Hyderabad (IN); Gundu Rao Padakandla, Hyderabad (IN); Mysore Aswatha Narayana Rao, Hyderabad (IN); Hari Babu Katta, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 205 days.

(21) Appl. No.: 13/081,054

(22) Filed: Apr. 6, 2011

(65) Prior Publication Data

US 2012/0197022 A1 Aug. 2, 2012

(30) Foreign Application Priority Data

Feb. 2, 2011 (IN) .............................. 313/CHE/2011

(51) Int. Cl.
*C07D 401/04* (2006.01)
(52) U.S. Cl. .................................................. 546/279.4
(58) Field of Classification Search ................ 546/279.4
See application file for complete search history.

(56) References Cited

PUBLICATIONS

Edward R. Bowman, et al., A Convenient Method for the Preparation of Racemic Nicotine, Department of Pharmacology, Medical College of Virginia, Virginia Commonwealth University, Richmond, Virginia 23298 and Department of Pathology, University of Miami School of Medicine, Miami, Florida 33101, 1982.
Pierre Dubon, Andreas Farwick, Gunter Helmchen, Enantioselective Syntheses of 2-Substituted Pyrrolidines From Allylamines by Domino Hydroformylation-Condensation: Short Syntheses of (S)-Nicotine and the Alkoloid 225C, Organisch-Chemisches Institut der Ruprecht-Karls-Universitat Heidelberg, Synlett 2009, No. 9 pp. 1413-1416.
R.B. Barlow and J. T. Hamilton, The Stereospecificity of Nicotine, From the Departments of Pharmacology of Edinburgh University and the University of Western Ontario, Canada, Brit. J. Pharmacol. (1965), 25, 206-212.
Mario D. Aceto, et al. Optically Pure (+)-Nicotine From (+)-Nicotine and Biological Comparisons With (−)-Nicotine, Department of Pharmacology, Medical College of Virginia, Richmond, Virginia 23298.
Jeffrey P. Jones, William F. Trager and Timothy J. Carlson, (S)-Nicotine With Cytochrome P-450CAM:Parallel Experimental and Theoretical Studies, Contribution from the Department of Pharmacology, University of Rochester, Rochester, New York 14642 and the Department of Medicinal Chemistry, University of Washington, Seattle, Washington 98195.
Lyman C. Craig, A New Synthesis of Nornicotine and Nicotine, Contribution from the Chemical Laboratory of the Johns Hopkins University, vol. 55, pp. 2854-2857, JACS, 1933.
Wilfried Hatton, et al. Synthesis of Four Racemic Nicotine Isotopomers Doubly Labelled With Stable Isotope, J. Label compd. Radiopharm 2009, pp. 117-122.
Teck-Peng Loh, et al. A Novel Reductive Aminocyclization for the Syntheses of Chiral Pyrrolidines:Stereoselective Syntheses of (S)-Nornicotine and 2-(2'-Pyrrolidyl)-Pyridines, Department of Chemistry, National University of Singapore, 10 Kent Ridge Crescent, Singapore 119260, Singapore, Tetrahedron Letters 40 (1999) 7847-7850.
Charles G. Chavdarian, Edward B Sanders, and Ronald L. Bassfield, Synthesis ofOptically Active Nicotinoids, Phillip Morris U.S.A. Research Center, Richmond, Virginia 23261.

*Primary Examiner* — Patricia L Morris
(74) *Attorney, Agent, or Firm* — Ceasar, Rivise, Bernstein, Cohen & Pokotilow, Ltd.

(57) ABSTRACT

(R,S)-Nicotine was resolved through diastereomeric salt formation using dibenzoyl-d-tartaric acid and dibenzoyl-l-tartaric acid to obtain enantiomerically pure (S)-nicotine and (R)-nicotine.

10 Claims, No Drawings

PROCESS FOR THE RESOLUTION OF (R,S)-NICOTINE

CROSS-REFERENCE TO RELATED APPLICATIONS

This application claims priority from India Application Serial No. 313/CHE/2011, filed on Feb. 2, 2011, entitled A PROCESS FOR THE RESOLUTION OF (R,S)-NICOTINE, which application is assigned to the same assignee as this application and whose disclosure is incorporated by reference herein.

FIELD OF INVENTION

The present invention describes a process for the preparation of (S) and (R)-nicotine through resolution of its racemic mixture prepared synthetically. The (S)-nicotine thus obtained is free from the related alkaloids such as anatabine, anabasine, cotinine, myosmine, β-nicotyrine, nornicotine etc., which are usually present as impurities in natural nicotine obtained from tobacco. The present invention also provides a process for preparing enantiomerically pure (R)-nicotine, which is otherwise difficult to obtain.

BACKGROUND OF THE INVENTION

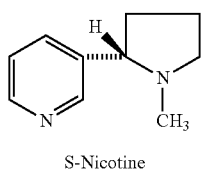

S-Nicotine

Nicotine is an alkaloid found mainly in tobacco and is chemically (S)-3-(1-methyl-2-pyrrolidinyl) pyridine. Smoking of tobacco results in nicotine dependence and is habit forming. Treating nicotine dependence in order to cease smoking requires therapeutic use of nicotine. Nicotine is administered to patients through dermal patches, gums, creams, lozenges, nasal sprays or electric cigarettes to wean them away from smoking. Nicotine is also therapeutically used in treating attention deficit disorder, Tourette's syndrome, schizophrenia, Alzheimer's disease, Parkinsonism, etc.

The main source of nicotine is tobacco. Nicotine isolated from tobacco contains many related minor alkaloids as impurities in addition to impurities formed through degradation. The European Pharmacopoeia monograph on nicotine describes anatabine, anabasine, cotinine, myosmine, β-nicotyrine, nicotine-N-oxide, and nornicotine as impurities which may be present in natural nicotine. The British Pharmacopoeia also mentions anatabine, cotinine, myosmine, β-nicotyrine, and nicotine-N-oxide as impurities.

The impurities present in nicotine vary depending on the geographical source of tobacco and the season in which it is collected. It is difficult to remove these impurities since they are chemically closely related and exhibit close physical properties. On the other hand, nicotine obtained from synthetic sources should be free from impurities present in natural nicotine. Further, synthetic nicotine produced by a validated process with a well characterized impurity profile is a superior API compared to natural nicotine with its varying impurity profile.

The first synthesis of optically active (S)-nicotine was reported by Charles G. Chavdarian., et al., (*J. Org. Chem.* 1982, 41, 1069-1073) using N-methyl-L-prolinol. (Scheme 1)

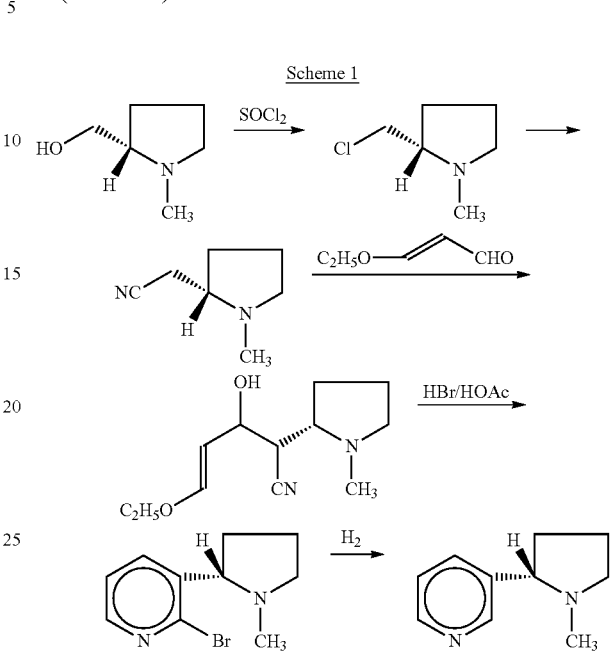

However, the optical purity of (S)-nicotine obtained was only 24%. The overall yield was also very poor. Stereoselective synthesis of (S)-nornicotine through reductive aminocyclization of 1,4-ketoaldehyde with pivaloyl-β-D-galactosylamine was reported by (Teck-peng., et al., *Tetrahedron Letters,* 1999, 40, 7847-7650) (Scheme 2). The so obtained (S)-nornicotine can be converted to (S)-nicotine by N-methylation.

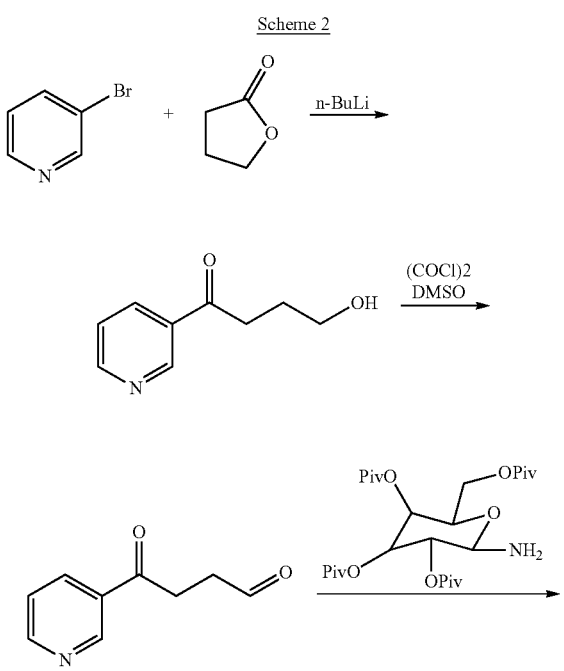

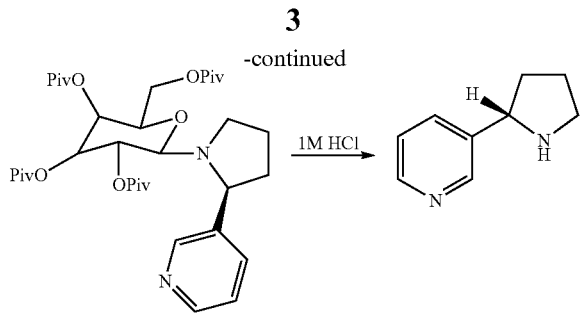

In scheme 2, the nitrogen of the chiral aminosugar is utilized to build the pyrrolidine ring system. The aminosugar is not regenerated in the process for recycling making the scheme expensive. Recently another asymmetric synthesis of S-nicotine was reported involving enantioselective amination of an allylic carbonate using an expensive rhodium biphephos chiral catalyst (Pierre Dubon., et al., *Synlett* 2009, 9, 1413-1416).

Since the enantioselective synthesis is also too expensive, it was thought that the resolution of racemic nicotine will be more economical. Further, it is possible to racemise the unwanted R-isomer (Bowman. E. R., et al., *Synthetic Communications*, 1982, 12, 871-879), which makes the process attractive.

The preparation of racemic nicotine is reported in the literature (Craig. L. C, et al. *J. Am. Chem. Soc.*, 1933, 55, 2854-2857). It can also be prepared by modifying methods reported for isotope labeled nicotine (Jones. J. P., et al., *J. Am. Chem. Soc.*, 1993, 105, 381-387); (Hatton. W., et al., *Label Compd. Radiopharm.* 2009, 52, 117-122). However, these methods are not suited for the commercial manufacture of (R,S)-nicotine. The present inventors have developed a commercially viable process for synthetic (R,S)-nicotine, which is the subject matter of another patent application. Thus, an acceptable source of racemic nicotine has become available to us.

Earlier efforts for resolving (R, S)-nicotine to obtain (R)-nicotine using l-tartaric acid were unsuccessful (Barlow and Hamilton, *Br. J. Pharmacol.*, 1965, 25, 206). Even after repeated crystallizations, optically pure (R)-nicotine could not be obtained. Several pharmacological activities reported for (R)-nicotine were based on optically impure samples (Aceto. M. D, et al., *J. Med. Chem.*, 1979, 22, 174-177). They isolated optically pure (R)-nicotine from (R, S)-nicotine using a combination of d-tartaric acid and dip-toluoyl-l-tartaric acid. The process is laborious and time consuming. First (R, S)-nicotine was treated with d-tartaric acid in a mixture of methanol and acetone. After 2 to 5 days, four crops of mainly (R)-nicotine di-d-tartrate were obtained. Treating the salt with ammonium hydroxide followed by extraction with diethyl ether gave (R)-nicotine which still contained appreciable amounts of (S)-nicotine. It was further treated with di-p-toluoyl-l-tartaric acid in acetone and the obtained diastereomeric salt contained optically pure (R)-nicotine. The authors have not reported any method to hydrolyze the salt to obtain (R)-nicotine. Bowman et al., reported the formation of (R)-nicotine di-p-toluoyl-l-tartrate and (S)-nicotine di-p-toluoyl-d-tartrate by treating (R, S)-nicotine with the corresponding di-p-toluoyl-tartaric acid in ethanol (Bowman. E. R., et al., *Synthetic Communications*, 1982, 12, 871-879). However, these salts were not hydrolyzed to obtain optically pure nicotine. Thus, most of the resolution studies are for obtaining (R)-nicotine, that are mainly for scientific studies. There are no reports for obtaining the natural isomer (S)-nicotine through resolution of the racemic base.

Although not intended to be bound thereby, one objective of the present invention is to provide an efficient process for obtaining enantiomerically pure (S)-nicotine through the resolution of (R, S)-nicotine using a suitable resolving agent.

Another objective of the present invention is to obtain enantiomerically pure (R)-nicotine through the resolution of (R, S)-nicotine using a suitable resolving agent.

Another objective is to develop a process for recovering the resolving agent without affecting its chemical chiral purity.

Yet another objective is to demonstrate a suitable racemization process for (R)-nicotine so that the whole process is commercially viable.

SUMMARY OF THE INVENTION

The present invention describes an efficient resolution of racemic nicotine to obtain enantiomerically pure (S) and (R)-nicotines using dibenzoyl-d-tartaric acid as a resolving agent. Efficient recovery of the resolving agent has also been achieved.

DETAILED DESCRIPTION OF THE INVENTION

Several resolving agents, solvents and their combinations were studied to resolve the synthetically obtained racemic nicotine. When the naturally available d-tartaric acid was used as the resolving agent, only the unnatural (R)-nicotine was obtained with low chiral purity (62%). When l-tartaric acid was used (S)-nicotine was obtained. Although its chiral purity was high (98.3%), the yield was very low (29%). When di-p-toluoyl-d-tartaric acid was used, (S)-nicotine was obtained in 60% yield with 88% chiral purity. When di-p-toluoyl-l-tartaric acid was used, (R)-nicotine was obtained in 15% yield with 94.7% chiral purity. In all the above cases, either the yield or the chiral purity was not satisfactory. We also studied dibenzoyl-d-tartaric acid as a resolving agent in different solvents (Table.1).

TABLE 1

Resolution of (R,S)-nicotine using dibenzoyl-d-tartaric acid:

| | | (S)-nicotine * | |
| --- | --- | --- | --- |
| S. No | Solvent | % Yield | % Chiral purity |
| 1 | Methanol | Nil | Nil |
| 2 | Ethanol | 36.4 | 96.4 |
| 3 | Isopropanol | ** | 55.7 |
| 4 | n-Butanol | ** | 63.2 |
| 5 | Acetonitrile | ** | 63.7 |
| 6 | Tetrahydrofuran | ** | 64.2 |
| 7 | Acetone | 37.2 | 93.9 |

* (R,S)-nicotine was treated with equivalent mol of dibenzoyl-d-tartaric acid in a solvent and the precipitated salt of (S)-nicotine di-benzoyl-d-tartrate was collected, salt was recrystallized using the same solvent and then hydrolyzed to obtain (S)-nicotine. The yield given is the final isolated yield and its chiral purity was measured by HPLC.
** In these solvents there was little selectivity and most of the salts of both (S) and (R)-nicotine precipitated out.

In ethanol, only (S)-nicotine salt precipitated out (96.4%), but the yields were low (36.4%). Acetone also gave similar results (94% chiral purity, 37.2% yield). Methanol did not give any crystalline material. Other solvents such as isopropanol, n-butanol, acetonitrile, and tetrahydrofuran were not useful.

We then studied a mixture of solvents in various proportions. Surprisingly, we found that a mixture of isopropanol and methanol is an excellent solvent system for the resolution of (S)-nicotine. (Table 2).

TABLE 2

Resolution of (R,S)-nicotine with dibenzoyl-d-tartaric acid in mixtures of isopropanol (IPA) and methanol (MeOH)

| Solvent | | (S)-nicotine* | |
|---|---|---|---|
| IPA | + MeOH | % Yield | % Chiral purity |
| 1.0 | 1.0 | 42.9 | 98.6 |
| 1.0 | 0.75 | 60.0 | 98.7 |
| 1.0 | 0.50 | 57.6 | 99.5 |
| 1.0 | 0.40 | 60.6 | 99.7 |
| 1.0 | 0.30 | 65.5 | 99.9 |
| 1.0 | 0.15 | 97 | 75 |

*(R,S)-nicotine was treated with equivalent mol of dibenzoyl-d-tartaric acid in solvent and the precipitated salt of (S)-nicotine di-benzoyl-d-tartrate was collected, the salt hydrolyzed and (S)-nicotine was obtained and its chiral purity measured by HPLC.

Although isopropanol and methanol individually were not satisfactory, their mixture was an excellent solvent system for the resolution giving (S)-nicotine selectively. Isopropanol-methanol in a ratio of 1.0:0.3 gave (S)-nicotine of very high chiral purity (99.9%) in very high yields (65.5%). When the methanol ratio was increased slightly, the chiral purity was not affected significantly but the yields were lower. When methanol ratio was decreased, the chiral purity also decreased.

When dibenzoyl-l-tartaric acid was used in place of dibenzoyl-d-tartaric acid, in a solvent system consisting of isopropanol-methanol in a ratio of 1.0:0.3, (R)-nicotine was obtained in 57.6% yield and showed a chiral purity of 99.9%. Other solvent combinations were also studied in an exhaustive manner. But, no other solvent system gave better results than isopropanol-methanol combination. Thus, it is not only the resolving agent, but also the selection of a suitable solvent system, which resulted in successful resolution of (R,S)-nicotine.

The process for (S)-nicotine consists of treating a solution of (R, S)-nicotine in isopropanol with dibenzoyl-d-tartaric acid. It is essential to stir the resulting suspension at least for an hour for complete salt formation. When the stirring time was decreased, the yields and the chiral purity were low. After stirring, the reaction mixture was heated and while refluxing, methanol was added to get a clear solution. Reflux was continued for about 10 minutes and cooled. After 1 hour, the precipitated salt of (S)-nicotine dibenzoyl-d-tartrate was collected by filtration. If the chiral purity is not satisfactory, the salt can be recrystallized using isopropanol-methanol (1:0.3) mixture. The salt can be hydrolyzed by either an acid or a base. We preferred an acid, especially hydrochloric acid, because one can recover dibenzoyl tartaric acid easily and in good yields (>90%) by extracting with ethyl acetate. Nicotine will remain in aqueous solution as hydrochloride salt. Using an alkali such as sodium hydroxide, free (S)-nicotine is released but remains in the solution. Several solvents were studied to extract (S)-nicotine from its aqueous solution. Best results were obtained with dichloromethane. With other solvents such as ethyl acetate, diisopropyl ether, ethylene dichloride, the yields were poor even after several extractions. Removal of the solvent gives pure (S)-nicotine. By a similar process, (R)-nicotine can be obtained by using dibenzoyl-l-tartaric acid.

A base such as sodium hydroxide can also be used for the hydrolysis of the salt of (S)-nicotine dibenzoyl-d-tartrate. Although (S)-nicotine could be obtained easily by extraction with dichloromethane, the alkaline condition caused ester hydrolysis of dibenzoyl-d-tartaric acid to a significant extent. Because of this hydrolysis recovery of dibenzoyl-d-tartaric acid was low.

The embodiments of the present invention are illustrated in the following examples, which are not intended in any way to limit the scope of the invention.

EXAMPLES

Example 1

A mixture of dibenzoyl-d-tartaric acid (58 g, 0.154 mol), 100 ml of isopropanol and (R,S)-nicotine (25 g, 0.154 mol) was stirred for 1 hr and heated to reflux. While refluxing, 30 ml methanol was added and refluxing continued for 10 min, cooled to room temperature and stirred for 1 hr. The salt of S-nicotine dibenzoyl-d-tartrate (31.3 g, 75.4%) so obtained was filtered. The salt was further recrystallized using isopropanol-methanol (1:0.3) mixture to obtain S-nicotine dibenzoyl-d-tartrate (28.6 g, 68.9% yield). The salt was treated with 10 ml water and 10 ml HCl, stirred for 10 min, extracted with ethyl acetate (50 ml×2) to recover dibenzoyl-d-tartaric acid. The aqueous layer was made alkaline using NaOH at 0° C. and extracted with dichloromethane (50 ml×4). Pooled dichloromethane extracts were dried over $Na_2SO_4$ and solvent evaporated completely to get an oily residue (8.5 g, 68% yield). This was purified by high vacuum distillation to get colorless pure (S)-nicotine (8.18 g, 65.5% yield, 99.85% GC, optical rotation: −140° (−130° to −143°, USP 31, 2008, p. 2801), 99.9% chiral purity by HPLC.

Example 2

A mixture of dibenzoyl-d-tartaric acid (58 g, 0.154 mol), 100 ml isopropanol and (R, S)-nicotine (25 g, 0.154 mol) was stirred for 1 hr and heated to reflux. While refluxing, 50 ml methanol was added, refluxing continued for 10 min, cooled to room temperature and stirred for 1 hr. The salt of S-nicotine dibenzoyl-d-tartrate (27.8 g, 66.9%) was filtered. The salt was further recrystallized using isopropanol-methanol (1:0.3) mixture to obtain S-nicotine dibenzoyl-d-tartrate (24.5 g, 59% yield). The salt was further treated as in example 1 to get (S)-nicotine (7.2 g, 57.6% yield) 99.85% GC, optical rotation: −137°, 99.5% chiral purity by HPLC.

Example 3

A mixture of di-p-toluoyl-d-tartaric acid (23.8 g, 0.0617 mol), 100 ml ethanol, and (R,S)-nicotine (10 g, 0.0617 mol) was stirred for 1 hr, refluxed for 15 min, cooled to room temperature and stirred for 1 hr. The salt was filtered and further recrystallized using ethanol to obtain S-nicotine di-p-toluoyl-d-tartrate (10.5 g, 62.1% yield). The salt was further treated as in example 1 to get (S)-nicotine (3 g, 60% yield) 87.9% chiral purity by HPLC.

Example 4

A mixture of dibenzoyl-d-tartaric acid (23.2 g, 0.0617 mol), 40 ml ethanol and (R,S)-nicotine (10 g, 0.0617 mol) was stirred for 1 hr, refluxed for 15 min, cooled to room temperature and stirred for 1 hr. The salt was filtered to obtain S-nicotine dibenzoyl-d-tartrate (7.2 g, 43.3% yield). The salt was further treated as in example 1 to get (S)-nicotine (1.82 g, 36.4% yield) 99.8% purity by GC, 96.4% chiral purity by HPLC.

Example 5

(R, S)-Nicotine (10 g, 0.0617 mol) was added to a solution of dibenzoyl-d-tartaric acid (23.2 g, 0.0617 mol) in 50 ml acetone, refluxed for 15 min, cooled to room temperature, stirred for 3 hrs and filtered to obtain the salt of S-nicotine dibenzoyl-d-tartrate (7.4 g 44.57% yield). The salt was hydrolyzed as in example 1 to get (S)-nicotine (1.86 g, 37.2% yield) 99.85% purity by GC, optical rotation: −121°, 93.9% chiral purity by HPLC.

Example 6

R-Nicotine

A mixture of dibenzoyl-l-tartaric acid (58 g, 0.154 mol), 100 ml isopropanol and (R,S)-nicotine (25 g, 0.154 mol) was stirred for 1 hr and heated to reflux. While refluxing, 50 ml methanol was added and continued as in Example 1 to get (R)-nicotine (7.2 g, 57.6% yield) 99.85% GC, optical rotation: +141°, 99.9% chiral purity by HPLC.

Example 7

Racemization of R-Nicotine

Sodium hydride (14.8 g, 0.616 mol of 60% dispersion in a mineral oil) was washed with toluene to remove the mineral oil and added to 100 ml of o-xylene. To this was added (R)-nicotine (10 g, 0.0617 mol). The reaction mixture was refluxed for 15 hrs, cooled to 0° C., the excess sodium hydride decomposed using dilute HCl (15%, 100 ml), the aqueous layer separated, the pH of the aqueous layer adjusted to >13 at 0° C. and extracted with dichloromethane. The solvent was then removed completely and the crude obtained was further purified by vacuum distillation at 0.1 mm Hg to get (R,S)-nicotine (6.68 g, 66.8% Y, 98.5% purity by GC, optical rotation: 0.8°)

We claim:

1. A process for the preparation of enantiomerically pure nicotine by the resolution of (R,S)-nicotine by diastereomeric salt formation using enantiomerically pure dibenzoyl tartaric acid as a resolving agent.

2. The process of claim 1 comprising:
a) dissolving (R, S)-nicotine in a polar solvent or a mixture of polar solvents and treating with enantiomerically pure dibenzoyl tartaric acid, to produce a precipitated salt of nicotine dibenzoyl tartrate;
b) filtering the precipitated salt of nicotine dibenzoyl tartrate;
c) hydrolyzing the salt using either an acid or a base;
d) extracting enantiomerically pure nicotine from the hydrolyzed reaction mixture of step (c) with an immiscible organic solvent; and
e) extracting enantiomerically pure dibenzoyl tartaric acid from the hydrolyzed reaction mixture of step (d) with an immiscible organic solvent.

3. The process as in claim 1 wherein the enantiomerically pure nicotine prepared is (S)-nicotine and the resolving agent used is dibenzoyl-d-tartaric acid.

4. The process as in claim 1 wherein the enantiomerically pure nicotine prepared is (R)-nicotine and the resolving agent used is dibenzoyl-l-tartaric acid.

5. The process as in claim 2 step-a, wherein the polar solvent is an aliphatic alcohol selected from the group consisting of methanol, ethanol, n-propanol, isopropanol, butanol or their mixtures.

6. The process as in claim 5, wherein the polar solvent is a mixture of isopropanol and methanol.

7. The process as in claim 2 step-d, wherein the immiscible organic solvent is selected from the group consisting of ethyl acetate, dichloromethane, diisopropyl ether and ethylene dichloride.

8. The process as in claim 7, wherein the solvent is dichloromethane.

9. The process as in claim 2 step-e, wherein the immiscible organic solvent is selected from the group consisting of ethyl acetate, diisopropyl ether, dichloromethane and ethylene dichloride.

10. The process as in claim 9, wherein the solvent is ethyl acetate.

* * * * *